United States Patent
Ariagno et al.

(10) Patent No.: US 11,033,459 B2
(45) Date of Patent: Jun. 15, 2021

(54) MODULAR VIAL ADAPTER

(71) Applicant: SHIRE HUMAN GENETIC THERAPIES, INC., Lexington, MA (US)

(72) Inventors: Scott Richard Ariagno, Inverness, IL (US); Daniel Edward Roush, Niles, IL (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 854 days.

(21) Appl. No.: 15/840,004

(22) Filed: Dec. 13, 2017

(65) Prior Publication Data
US 2018/0161243 A1  Jun. 14, 2018

Related U.S. Application Data

(60) Provisional application No. 62/433,512, filed on Dec. 13, 2016.

(51) Int. Cl.
*A61J 1/20* (2006.01)
*A61J 1/14* (2006.01)
(Continued)

(52) U.S. Cl.
CPC .............. *A61J 1/2065* (2015.05); *A61J 1/14* (2013.01); *A61J 1/1475* (2013.01); *A61J 1/20* (2013.01);
(Continued)

(58) Field of Classification Search
CPC ........ A61J 1/2065; A61J 1/201; A61J 1/2072; A61J 1/2075; A61J 1/2082; A61J 1/2086;
(Continued)

(56) References Cited

U.S. PATENT DOCUMENTS

| 5,526,853 | A | 6/1996 | McPhee et al. |
| 8,512,309 | B2 | 8/2013 | Shemesh et al. |

(Continued)

FOREIGN PATENT DOCUMENTS

| JP | 2012-135439 A | 7/2012 |
| WO | 2014/003614 A1 | 1/2014 |

(Continued)

OTHER PUBLICATIONS

International Search Report and Written Opinion dated Mar. 30, 2018, for application PCT/US2017/065967, filed Dec. 13, 2017 (9 pages).

(Continued)

*Primary Examiner* — Philip R Wiest
(74) *Attorney, Agent, or Firm* — Troutman Pepper Hamilton Sanders LLP (57) ABSTRACT

The present disclosure is directed to a vial adapter for interconnecting a vial and a fluid delivery device, and, more particularly, to a vial adapter having a modular design consisting of separately constructed components cooperatively arranged and coupled to one another. The modular construction allows for rapid manufacturing reconfigurations of one or more components with minimal costs to create new vial adapter configurations that meet specific needs.

16 Claims, 4 Drawing Sheets

(51) Int. Cl.
   *A61M 5/162* (2006.01)
   *A61M 39/10* (2006.01)
(52) U.S. Cl.
   CPC ............. *A61J 1/201* (2015.05); *A61J 1/2072* (2015.05); *A61J 1/2082* (2015.05); *A61J 1/2086* (2015.05); *A61M 5/162* (2013.01); *A61M 39/10* (2013.01)
(58) Field of Classification Search
   CPC .. A61J 1/14; A61J 1/1475; A61J 1/20; A61M 5/162; A61M 39/10
   See application file for complete search history.

(56) References Cited

U.S. PATENT DOCUMENTS

| | | | |
|---|---|---|---|
| 10,201,476 B2* | 2/2019 | Fangrow | A61J 1/1406 |
| 2014/0261860 A1 | 9/2014 | Heath et al. | |
| 2015/0283032 A1* | 10/2015 | Lin | A61M 5/3202 604/406 |
| 2016/0271017 A1* | 9/2016 | Weir | A61J 1/2055 |
| 2017/0095404 A1* | 4/2017 | Fangrow | A61J 1/2086 |

FOREIGN PATENT DOCUMENTS

| | | |
|---|---|---|
| WO | 2014/041529 A1 | 3/2014 |
| WO | 2015/067548 A1 | 5/2015 |

OTHER PUBLICATIONS

Extended European Search Report issued in corresponding European Patent Application No. 17879922.7 dated Jun. 17, 2020.

* cited by examiner

MODULAR VIAL ADAPTER

CROSS-REFERENCE TO RELATED APPLICATIONS

This application claims the benefit of, and priority to, U.S. Provisional Application No. 62/433,512, filed Dec. 13, 2016, the content of which is hereby incorporated by reference herein in its entirety.

FIELD

The present disclosure relates generally to a vial adapter for interconnecting a vial and a fluid delivery device, and, more particularly, to a vial adapter having a modular design consisting of separately constructed components cooperatively arranged and coupled to one another.

BACKGROUND

Drug vials are routinely used in hospitals and other medical settings for storing medications in the form of liquids and powders. A drug vial generally includes a glass or plastic container and a closure for containing fluid content within. The closure is typically formed of metal crimped over a rubber stopper and a flange, so as to positively hold the stopper in place over the opening of the vial. The rubber stopper, generally formed of an elastomeric material such as butyl rubber or the like, is pierceable, allowing for a user to gain access to the fluid content. For example, in order to access the contents within the vial, a user typically uses a syringe fitted with a needle to pierce the rubber stopper of the vial and withdraw the fluid. However, such methods of obtaining the contents from the vial present drawbacks, such as accidental sticking with the needle or leakage of the fluid by way of a gap between the needle and the rubber stopper. The leakage of fluid may result in inaccurate withdrawal and subsequent administration of the medication, which can lead to ineffective treatment. The inadvertent fluid leakage may be particularly troublesome when the liquid chemical is a hazardous drug, such as a carcinostatic agent, wherein inadvertent leakage of can put the user, such as a health care provider or patient, at risk of exposure to these medications.

In an attempt to address the drawbacks of conventional needle withdrawal, vial adapters have been introduced to permit drug preparation and withdrawal. Vial adapters generally include a fitting portion having claws or the like for fitting a vial therein, a metallic or resin made (plastic-made) needle provided with a liquid passage, and a connector for connection to a syringe or other fluid delivery device, wherein the fitting portion, needle, and connector are integrally formed with one another as a single unit. Although current adapters allow for the withdrawal of fluid content from vials, such adapters suffer from various shortcomings.

For example, vials are available in a range of sizes, including, but not limited to 8 mm, 11 mm, 13 mm, 17 mm, 20 mm, 28 mm, and 32 mm closure openings, as well as varying thickness of the stopper feature. Most adapters, however, are designed to function only on a single vial closure size. Accordingly, some current adapters, which are manufactured to fit a specific vial closure size, fail to securely attach to vial closures having diameters that are outside of their tolerance (i.e., smaller or larger than the vial closure size that such adapters are intended to fit). Accordingly, the use of current adapters is limited to the size of vial for which they were manufactured. A further consideration is the expense incurred by hospitals or other medical facilities as a result of the need to stock various types and sizes of adapters. For example, there is generally no universal vial size, as different medications and treatment are provided in varying doses. Thus, vials of many flange sizes and closure sizes are available and are frequently found in medical care facilities. Typically a hospital must stock a variety of adapters to be assured of having the correct adapter available that will properly interconnect with the multiple vial closures that exist. Thus, a hospital must maintain a stock of adapters for each possible size of closure, resulting in a logistical problem, as well as increased expense.

SUMMARY

The present invention is directed to a vial adapter for interconnecting a vial and a fluid delivery device or apparatus. The vial adapter has a modular design consisting of separately constructed components cooperatively arranged with one another. The modular construction allows for rapid manufacturing reconfigurations of one or more components with minimal costs to create new vial adapter configurations that meet specific needs. In particular, the present invention includes separately formed (i.e., separately manufactured) components which, when assembled to one another, form a fully functional vial adapter configured to engage a vial, including fluid content therein, and further interconnect the vial with a delivery device, such as a syringe or, in some instances, an injector or pump assembly (e.g., infusion device).

The modular vial adapter of the present disclosure generally includes a spike member including a distal tip configured to engage and penetrate a seal provided on a closure of the vial for access to fluid content within. The spike member may include a dual-lumen design, in which at least a first lumen in communication with the distal tip providing a fluid pathway through the spike member for transport of fluid content from the vial while a second lumen provides a venting pathway allowing atmospheric air to enter an interior space of the vial to prevent negative pressure buildup.

The vial adapter further includes a separately formed port member configured to be directly coupled to the spike member. The port member includes a channel extending therethrough and in communication with the fluid pathway of the first lumen of the spike member to receive the fluid content from the vial. The port member further includes a connecter assembly configured to be releasably coupled to the delivery device and to provide fluid content via the channel. For example, the connector assembly may include a Luer-Lock or Luer-Slip connection fitting configured to be releasably coupled to a delivery device having a corresponding Luer-Lock or Luer-Slip connection fitting. In some embodiments, the connector assembly may include a delivery device-specific connection fitting, wherein the delivery device comprises a pump and/or injector assembly, such as an infusion pump.

The vial adapter further includes a separately formed skirt member configured to be coupled to and retain at least a portion of each of the spike member and port member. The skirt member includes a cavity shaped and/or sized to receive and engage the closure of the vial within. Upon positioning of the vial closure within the cavity (i.e., upon a user placing the vial into engagement with the adapter), the distal tip of the spike member is configured to penetrate the seal of the vial and fluid content within the vial is available for transfer to the delivery device via the fluid pathway from the distal tip of the spike member through the channel of the port member and out of the connecter assembly of the port member.

The vial adapter of the present disclosure allows for the interchangeability of components to provide numerous combinations of a vial adapter to thereby to accommodate the varying vial flange and closure sizes currently offered, as well as other variations, such as the type of delivery device to be used and the specific contents provided in the vial. In particular, depending on the specific needs or requirements, individual components can be swapped out and changed to account for different vial closure sizes, different thicknesses of the rubber stop, different connection fittings required depending on the delivery device to be used, and the like. For example, in order to account for different vial closure sizes (i.e., diameters of the vial closure), the skirt member may be interchangeable with one of a plurality of other skirt members (while the spike member and port member configurations remain the same), wherein the plurality of other skirt members may include different dimensions (e.g., cavities with different volumes). In order to account for different delivery devices to be used with the adapter, the port member may be interchangeable with one of a plurality of other port members (while the spike member and skirt member configurations remain the same), wherein the plurality of other port members may include different connector assembly connection fittings (e.g., Luer-Lock fitting, Luer-Slip fitting, push-to-connect fitting, Interlink-style bayonet or septum fitting, etc.). In order to control the flow rate of fluid content from the vial, the spike member may be interchangeable with one of a plurality of other spike members (while the port member and skirt member configurations remain the same), wherein the plurality of other spike members may include different venting assemblies (e.g., vent filters of different pore size to control rate of flow of fluid content from the vial, to control ingress of various size particles, or to control egress of fluid under pressure).

Accordingly, the modular vial adapter of the present invention addresses the shortcomings of current vial adapters. The modular design, consisting of separately constructed components cooperatively arranged with one another, allows for rapid manufacturing reconfigurations of one or more components with minimal costs to create new vial adapter configurations that meet specific needs, thereby benefitting both end-users and manufacturing strategy. In particular, individual components can be swapped out and changed to depending on the specific needs or requirements, which may include, for example, different vial closure sizes, different thicknesses of the rubber stop, different connection fittings required depending on the delivery device to be used, and the like.

BRIEF DESCRIPTION OF THE DRAWINGS

Features and advantages of the claimed subject matter will be apparent from the following detailed description of embodiments consistent therewith, which description should be considered with reference to the accompanying drawings.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

The present invention is directed to a vial adapter for interconnecting a vial and a fluid delivery device or apparatus. The vial adapter has a modular design consisting of separately constructed components cooperatively arranged with one another. In particular, the present invention includes separately formed (i.e., separately manufactured) components which, when assembled to one another, form a fully functional vial adapter configured to engage a vial, including fluid content therein, and further interconnect the vial with a delivery device, such as a syringe or, in some instances, an injector or pump assembly (e.g., infusion device). The modular construction allows for rapid manufacturing reconfigurations of one or more components with minimal costs to create new vial adapter configurations that meet specific needs.

Figure 1:
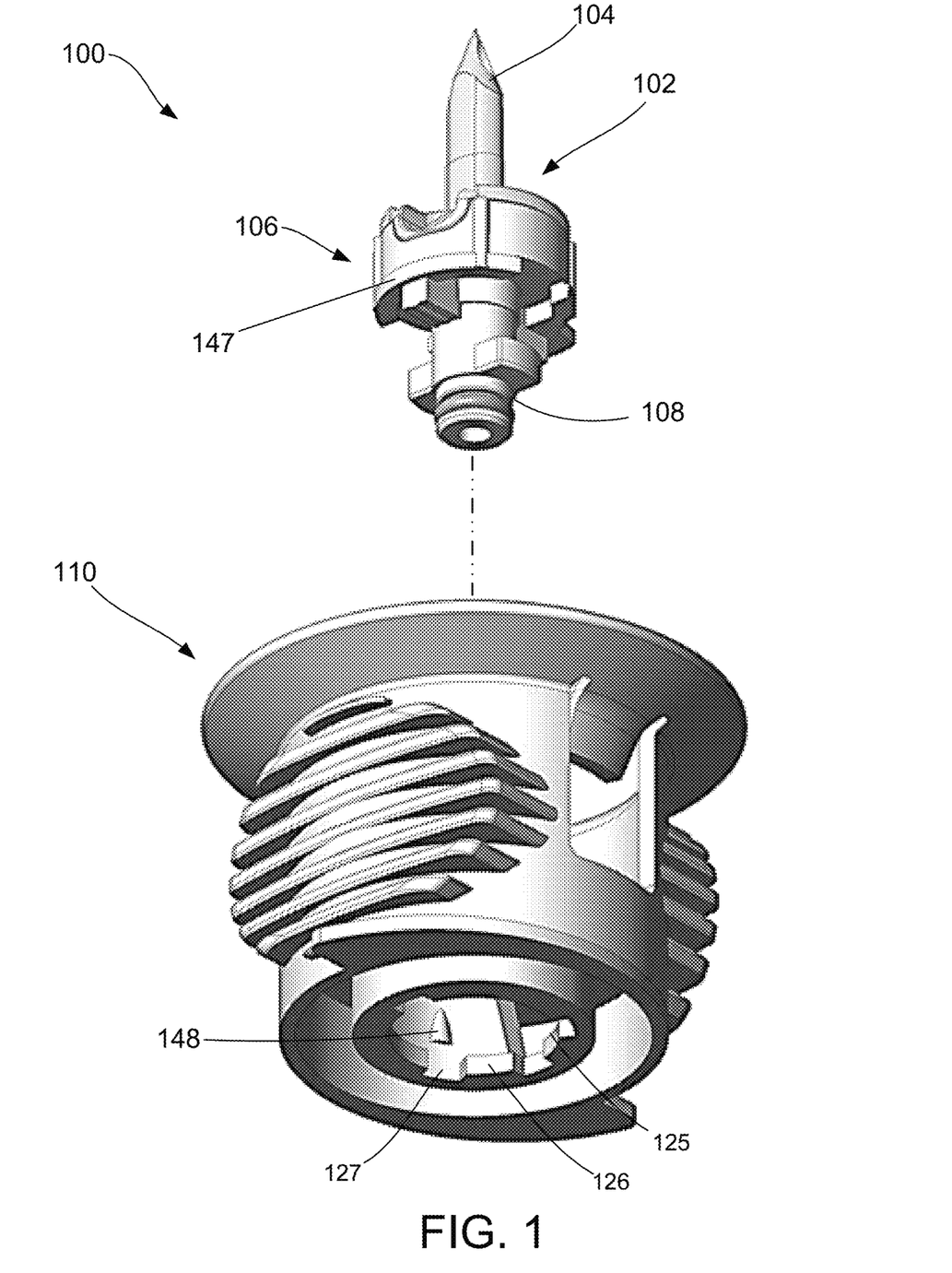
FIG. 1 is an exploded perspective view of a modular vial adapter of the present disclosure, illustrating a spike member and port member assembled to one another and separated from a skirt member.
Figure 2:
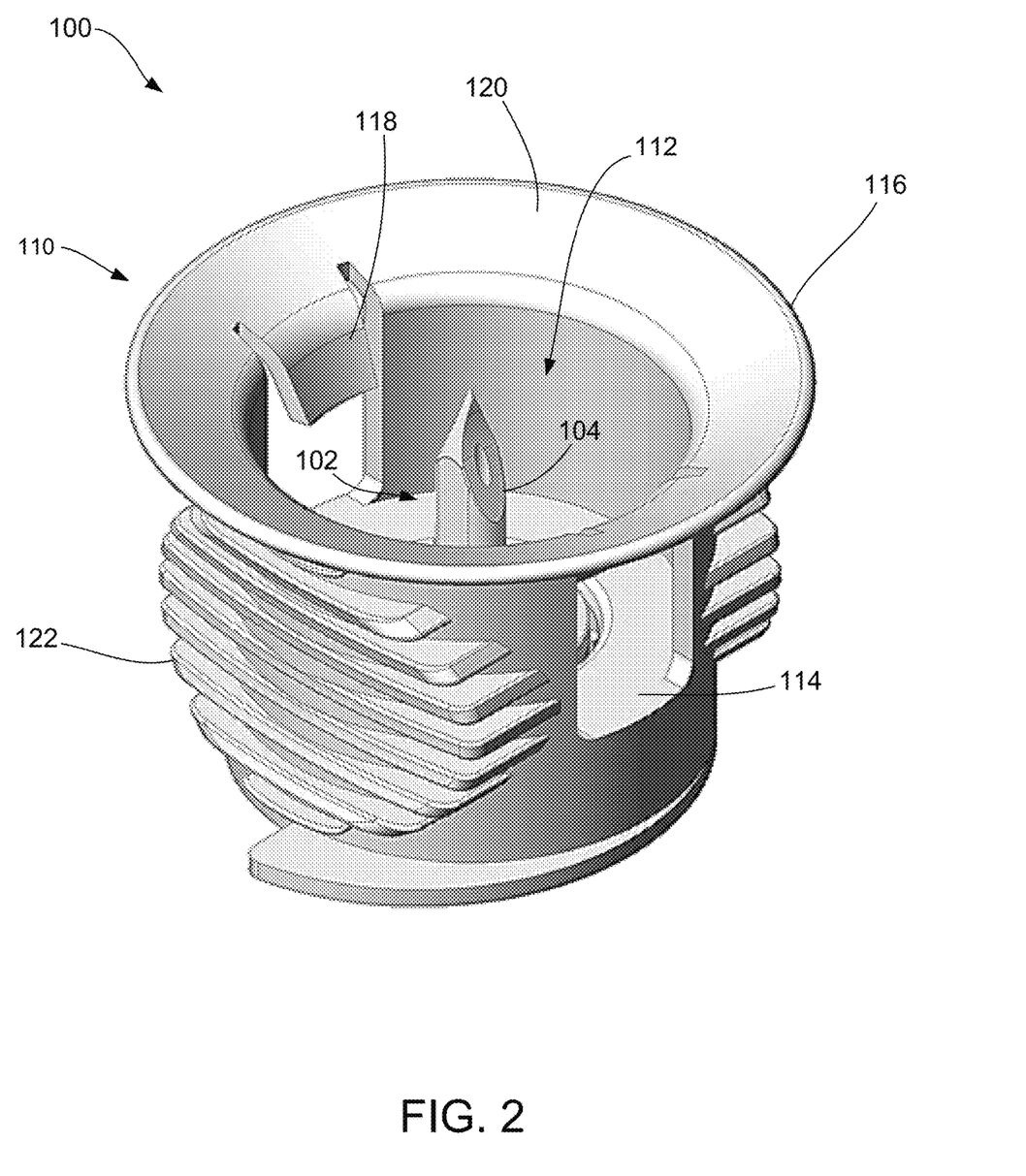
FIG. 2 is a perspective view of the modular vial adapter of FIG. 1 illustrating the components assembled with one another.

FIG. 1 is an exploded perspective view of a modular vial adapter 100 consistent with the present disclosure illustrating some components separated from one another while FIG. 2 is a perspective view of the modular vial adapter 100 illustrating the adapter in a fully assembly state.

As will be described in greater detail herein, the modular vial adapter 100 is configured to interconnect a vial with a delivery device. The vial (not shown) may generally include the standard vial closure, which may include, for example, a stopper (rubber stopper) formed of an elastic material and operative to seal a flange of the vial body in an airtight manner, and a cap that covers outer circumferences of the flange of the vial body and stopper. The cap is formed, for example, from a soft metal such as aluminum, with an opening provided on an upper surface thereof. An upper surface of the stopper is exposed through the opening. The cap covers an outer circumferential surface of the stopper, an upper surface edge portion of the stopper, an outer circumferential surface of the flange, and a lower surface edge portion of the spout. As described herein, the vial adapter 100 is configured to receive at least a head portion of the vial, which may include a portion of the flange of the vial body, the stopper, and the cap. The delivery device (not shown) may include any type of device or apparatus for delivering the fluid content within the vial, including, but not limited to, syringes, pumps, injectors, and the like.

As shown in FIGS. 1 and 2, the modular vial adapter 100 generally includes a spike member 102 including a distal tip 104 configured to engage and penetrate a seal provided on a closure of the vial for access to fluid content within. As will be described in greater detail herein, the spike member 102 includes a dual-lumen design, which includes at least a first lumen in communication with the distal tip 104 and providing a fluid pathway through the spike member 102 for transport of fluid content from the vial, and a second lumen in communication with the distal tip 104 and providing vent pathway allowing atmospheric air to enter an interior space of the vial to prevent negative pressure buildup during transport of fluid content from the vial through the fluid pathway of the first lumen. The distal tip 104 is generally in the form of an off-center tip, beveled in such a manner so as to provide improved penetration through the rubber stopper (with as little resistances as possible). In particular, the lumen diameters, tip bevel geometry, and oval profile may be optimized to minimize insertion force, prevent stopper coring, and minimize residual fluid loss.

The spike member 102 may be formed from a thermoplastic polymer material, such as acrylonitrile butadiene styrene (ABS), for example. It should be noted that the spike member 102 may be formed from any other suitable medical-grade material and is not limited to ABS. Additionally, or alternatively, a small amount of medical-grade lubricant, such as 0.5 to 2.5 mg of Dow 360, can be applied near the penetrating tip. The use of lubricant may reduce stopper penetration force that must otherwise be generated by an end-user. The lubricant improves consistency of stopper deformation to further minimize residual fluid loss and reliance on user technique.

The vial adapter 100 further includes a separately formed port member 106 configured to be directly coupled to the spike member 102. In particular, the spike member 102 and port member 106 may be fixed via an adhesive or ultrasonic welding, for example. As will be described in greater detail herein, the port member 106 generally includes a channel extending therethrough and in communication with the fluid pathway of the first lumen of the spike member 102 to thereby receive the fluid content from the vial. As shown in FIGS. 1 and 2, the port member 106 further includes a connecter assembly 108 configured to be releasably coupled to a delivery device and to provide fluid content thereto via the channel. For example, the connector assembly 108 may include a conventional Luer-Lock or Luer-Slip connection fitting configured to be releasably coupled to a delivery device having a corresponding Luer-Lock or Luer-Slip connection fitting. However, as shown, the connector assembly 108 may include a delivery device-specific connection fitting, wherein the delivery device comprises a pump and/or injector assembly, such as an infusion pump. For example, in the illustrated embodiment, the connector assembly 108 may be configured to connect with a corresponding connection fitting of wearable infusion platforms and devices, such as, for example, infusion devices offered by Sensile Medical AG (Hägendorf, Switzerland).

The vial adapter 100 further includes a separately formed skirt member 110 configured to be coupled to and retain at least a portion of each of the spike member 102 and port member 106. For example, as shown in FIG. 2, the skirt member 110 includes a cavity 112 generally defined by a base 114 and at least one side wall 116 extending therefrom and terminating at an open distal end to define the cavity 112. The spike member 102 and port member 106 are positioned and retained within a recess defined on the base 114, as will be described in greater detail herein. The cavity 112 is generally shaped and/or sized to receive and engage the closure of the vial within. For example, the at least one wall 116 is generally cylindrical and corresponds to the convention cap design. The cylindrical wall 116 generally ensures that the vial is centered with the spike member 102 so as to confirm a straight distal tip 104 penetration into the vial. The skirt member 110 may include an angled lead-in 120 along the periphery of the open end, so as to aid a user with initial alignment.

The skirt member further includes a pattern of detents 118 configured to engage a portion of the cap, specifically the underside of the flange of the vial to retain the head of the vial within the cavity 112 once positioned therein. The pattern of detents 118 may be positioned a specific distance from the base 114 so as to account for the distal tip 104 penetration depth relative to the stopper. The detent 118 geometry can be adjusted to achieve tactile/audible user feedback of complete docking and to either allow or prevent vial removal. The skirt member 110 may further include one or more grip portions 122 on an external surface to provide improved handling for the end-user.

The skirt member 110 generally has no fluid contact and thus requires far less molding precision than the spike member 102 or port member 106, which allows for wider choice of polymers, processing windows, and production tooling.

Figure 3:
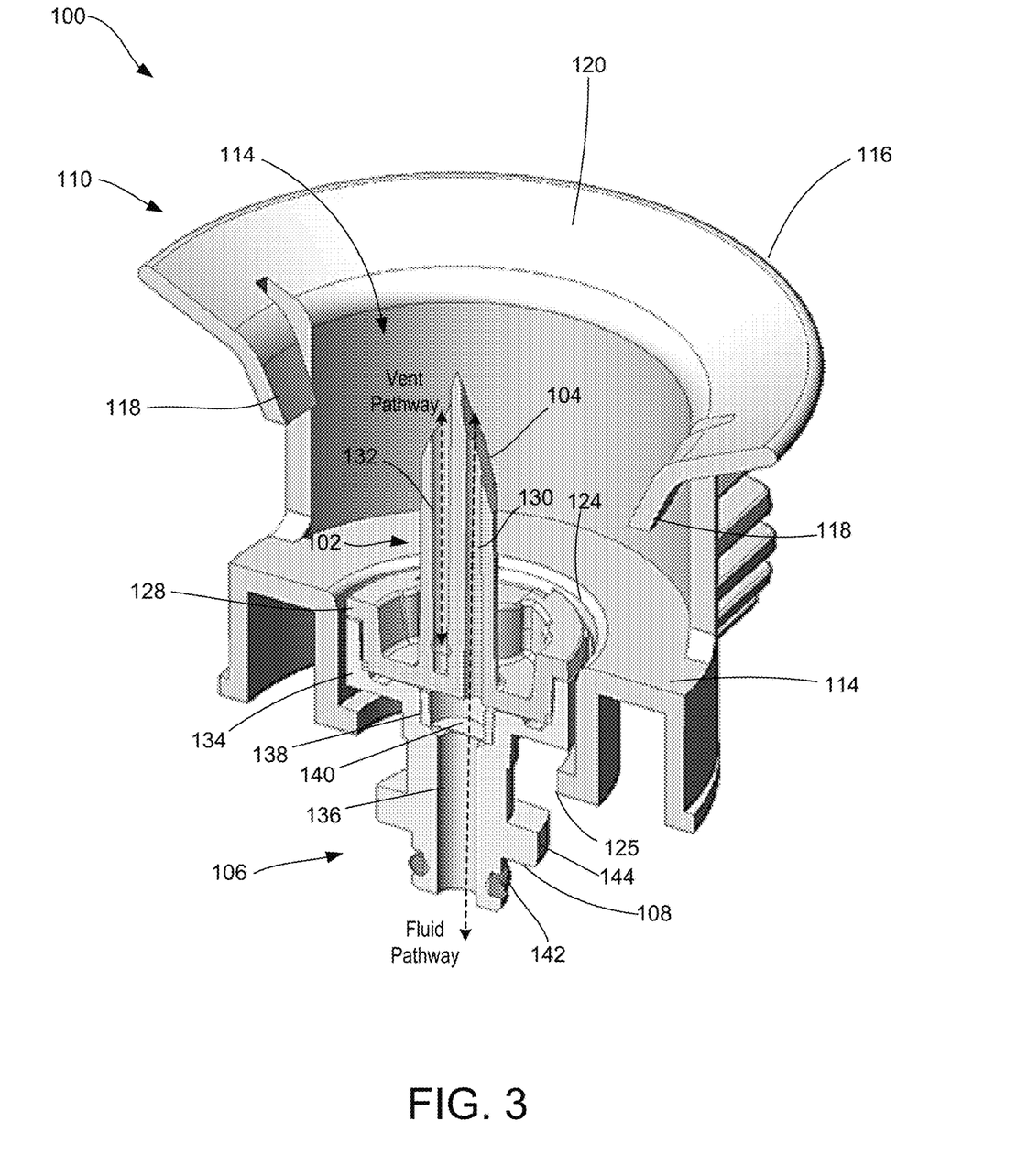
FIG. 3 is a perspective cross-sectional view of the modular vial adapter in an assembled state.
Figure 4:
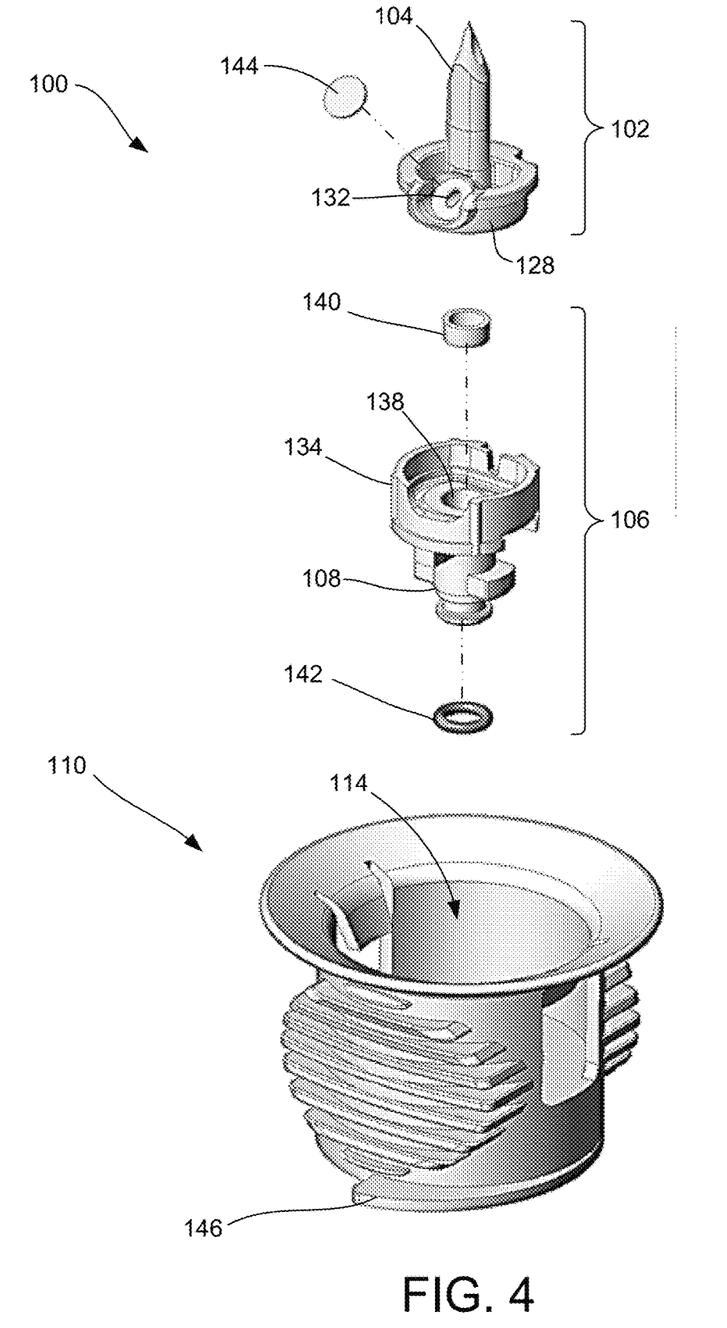
FIG. 4 is a fully exploded perspective view of a module vial adapter consistent with the present disclosure.

FIG. 3 is a perspective cross-sectional view of the modular vial adapter 100 in an assembled state. FIG. 4 is a fully exploded perspective view of a module vial adapter consistent with the present disclosure. As shown, the base 114 within the cavity 112 of the skirt member 110 includes a recess 124 having a bore 125 extending therethrough. The recess 124 is configured to receive and retain portions of the spike member 102 and port member 106 therein. The recess 124 generally holds the spike member 102 and port member 106 in place by a simple snap-fit design at defined protrusions extending inwardly from an interior surface of the recess 124. Upon insertion of the spike member 102 and port member 106 into skirt member 110, a pattern of detents 148 in skirt member 110 as shown in FIG. 1 are deflected outward by flange 147 on port member 106, and then snap back over flange 147 upon complete insertion to irreversibly capture spike member 102 and port body member 106 inside of cavity 112 of skirt member 110. The bore 125, through which the connector assembly 108 passes, is configured to maintain vertical position of the spike member 102 and port member 106 in part by planar positive stop features 126 and radial cuts 127, in which a corresponding pattern of external features of the port member 106 interact so as to prevent rotation.

Upon positioning of the head portion of the vial within the cavity 112, which may include a portion of the flange of the vial body, the stopper, and the cap, the distal tip 104 of the spike member 102 is configured to penetrate the seal of the vial. As the vial is pressed further into the cavity 112, the detents 118 engage the underside of the flange of the vial to maintain the head within the cavity 112 and prevent unwanted withdraw. Once the head of the vial is positioned within the cavity 112, the fluid content within the vial is available for transfer to the delivery device through the spike member 102 and port member 106. In particular, as shown in FIG. 3, the spike member 102 includes a base 128 from which the distal tip 104 extends. The base 128 is sealed to a corresponding base 134 of the port member 106, thereby completing a fluid pathway from the distal tip 104 through the spike member 102 and the port member 106 to the connector assembly 108. As shown, the spike member 102 has at least a first lumen 130 in communication with the distal tip 104 and providing a fluid pathway through the spike member 102 for transport of fluid content from the vial. The spike member 102 further includes a second lumen 132 separate from the first lumen 130 and in communication with the distal tip 104. The second lumen 132 provides a vent pathway for allowing atmospheric air to enter an interior space of the vial to prevent negative pressure buildup when fluid content is transported from the vial via the fluid pathway provided by the first lumen 130. For example, the second lumen 132 includes a first open end positioned at the distal tip and a second open end positioned at a base 128 of the spike member 102 (see FIG. 4). As shown in FIG. 4, a vent filter 144 may be coupled to the second open end of the second lumen. The filter may include a hydrophobic material having a pore size of approximately 0.1 microns to 5 microns. The vent filter 144 may be ultrasonically welded onto 45-degree surface of the base 128 of the spike member 102 where the second opening of the second lumen 132 is located. In one embodiment, vent filter material may include a hydrophobic and oleophobic membrane, such as Pall Versapor 3000R. Such a membrane with 3 micron pore size is already qualified as a static microbial barrier that effectively resists liquid leakage (approximately 2 PSI water breakthrough pressure). It should be noted that inadvertent exposure to silicone lubricant will not block this membrane's pores.

Figure 5:
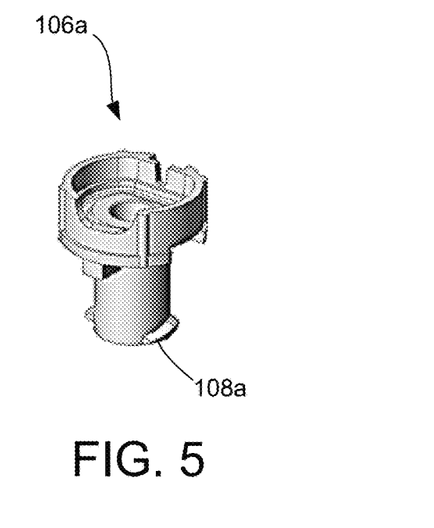
FIG. 5 is a perspective of an alternative port member having a different connector assembly configured with a Luer-type fitting connection.

Referring to FIG. 3, once coupled to the spike member 102, the channel 136 of the port member 106 is in alignment with the first lumen 130 of the spike member 102 and thus in communication with the fluid pathway and provides a pathway for fluid content from the vial, which extends through the connector assembly 108 and into a device coupled thereto. The channel 136 of the port member 106 further includes a channel opening 138 formed on a distal end thereof opposite the connector assembly 108, wherein the channel opening 138 is shaped and/or sized to receive and retain a fluid filter membrane 140 within. The solution filter membrane 140 is configured to filter fluid content and/or moderate flow rate passing through the channel 136. The filter 140 may include a material having a pore size of approximately 5 microns to 150 microns. As shown, the solution filter 140 is welded or overmolded to a semi-rigid elastomeric ring that is press-fit into the channel opening 138. As shown, the connector assembly 108 is configured for use with a Sensile Medical infusion device. Accordingly, the connector assembly 108 may include an external elastomeric seal 142 in addition to opposing tabs 144 that operate a valve within the Sensile Wearable Infusor device. However, as previously noted, the connector assembly 108 may include other types of connection fittings, such as the Luer-type fitting connection 108a illustrated in FIG. 5.

The skirt member 110 may further include external protrusions 146 added to the port-end (far opposite of vial opening), which are a unique feature not seen in other commercial vial adapters. Such protrusions 146 can engage with mating geometry of another device for purposes of alignment and limiting rotation by positive stop. For example, the Sensile pump requires that a vial adapter be inserted in a specific starting orientation and that vial adapter be rotated exactly 90 degrees to operate an internal valve mechanism. The protrusions 146 provide an easily visible, robust tactile (and possibly even audible) feedback to help end-user connect vial adapter to Sensile pump correctly.

The vial adapter of the present disclosure allows for the interchangeability of components to provide numerous combinations of a vial adapter to thereby to accommodate the varying vial flange and closure sizes currently offered, as well as other variations, such as the type of delivery device to be used and the specific contents provided in the vial. In particular, depending on the specific needs or requirements, individual components can be swapped out and changed to account for different vial closure sizes, different thicknesses of the rubber stop, different connection fittings required depending on the delivery device to be used, and the like. For example, in order to account for different vial closure sizes (i.e., diameters of the vial closure), the skirt member may be interchangeable with one of a plurality of other skirt members (while the spike member and port member configurations remain the same), wherein the plurality of other skirt members may include different dimensions (e.g., cavities with different volumes). In order to account for different delivery devices to be used with the adapter, the port member may be interchangeable with one of a plurality of other port members (while the spike member and skirt member configurations remain the same), wherein the plurality of other port members may include different connector assembly connection fittings (e.g., Luer-Lock fitting, Luer-Slip fitting, push-to-connect fitting, Interlink-style bayonet or septum fitting, etc.). In order to control the flow rate of fluid content from the vial, the spike member may be interchangeable with one of a plurality of other spike members (while the port member and skirt member configurations remain the same), wherein the plurality of other spike members may include different venting assemblies (e.g., vent filters of different pore size to control rate of flow of fluid content from the vial).

Yet further still, other changes/modifications could be made to the spike member, port member, and/or skirt member. For example, the spike member may include changes such as smaller and circular spike profile area, smaller lumen sizes, lumen opening placement beside a center-point tip, thinner walls, and stiffer material. In some embodiments, a pierceable elastomeric sheath could be placed over the spike to close the fluid path (i.e. prevent particulate from entering the fluid path). The spike member and port member material can be changed from ABS to other rigid polymers, such as polycarbonate and cyclic olefin polymer (COP), which are both weldable. COP has low absorption rate property that can minimize residual sterilants like VHP and minimize interaction with drug/biologic solutions. The seal of Sensile-compatible port could be integral 2-shot molded seal instead of the assembled o-ring. Additional port geometries include locking or slip male luer, male luer lock with free-spin collar, male or female luer activated device (LAD), push-to-connect fitting, Interlink-style bayonet or septum, or new custom (tamper proof) connector. The solution filter pore size could be adjusted between approximately 5 microns to 150 microns to balance particulate removal efficiency needs with design/user tolerance for flow resistance. The solution filter may be welded directly into the port component, rather than attached to a press-fit ring. Depth filters, such as Porex porous disks, could be directly press fit into the port well rather than membrane filters. As an alternative, the filter 140 might be replaced with a disk with a central orifice sized to moderate the flow rate of fluid passing through channel 136. The filter might also be replaced by a one-way check valve, as in an elastomeric duckbill or a spring loaded ball check valve assembly, to provide one directional flow to prevent fluid from being forced back into the vial assembly. Also, the solution filter could be completely eliminated. The skirt could be modified to mimic the "diluent sleeve and washer" of BAXJECT III, which, when including the Vaporized Hydrogen Peroxide decontamination step, would allow vial adapters to be pre-connected to vials without flip caps during manufacturing. End users would receive and all-in-one system that is ready to activate in a single motion (fewer steps, faster, mistake proof).

Accordingly, the modular vial adapter of the present invention addresses the shortcomings of current vial adapters. The modular design, consisting of separately constructed components cooperatively arranged with one another, allows for rapid manufacturing reconfigurations of one or more components with minimal costs to create new vial adapter configurations that meet specific needs, thereby benefitting both end-users and manufacturing strategy. In particular, individual components can be swapped out and changed to depending on the specific needs or requirements, which may include, for example, different vial closure sizes, different thicknesses of the rubber stop, different connection fittings required depending on the delivery device to be used, and the like.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof

What is claimed is:

1. A modular vial adapter for interconnecting a vial with a delivery device, the modular vial adapter comprising:
    a spike member comprising a base and a distal tip extending therefrom, the spike member further comprising at least:
        a first lumen extending from the base to the distal tip and providing a fluid pathway therethrough; and
        a second lumen separate from the first lumen and having a first open end proximate the base and a second open end proximate the distal tip, the first open end being positioned external to the modular vial adapter such that the second lumen provides a vent pathway for allowing atmospheric air to enter an interior space of the vial to prevent negative pressure buildup when fluid content is transported from the vial via the fluid pathway of the first lumen;
    a separately formed port member comprising a first end defining a base directly coupled to the base of the spike member and an opposing second end defining a connector assembly, the port member further comprising a channel extending therethrough from the first end to the second end and in fluid communication with the fluid pathway of the first lumen of the spike member upon coupling of spike member base with the port member base; and
    a separately formed skirt member comprising a proximal end defining a base including a recess having a bore extending therethrough, wherein the recess is shaped and/or sized for receiving and retaining portions of the spike member and port member therein, the skirt member further comprising at least one side wall extending from the base and terminating at an open distal end to define a cavity shaped and/or sized to receive and engage a closure on a vial,
    wherein, upon positioning of a vial closure within the cavity of the skirt member, the distal tip of the spike member is configured to penetrate a seal of the vial and fluid content within the vial is available for transfer to a delivery device releasably coupled to at least the connector assembly of the port member via the fluid pathway from the distal tip of the spike member through the channel of the port member and out of the connecter assembly of the port member, and
    wherein, when the spike member, port member, and skirt member are unassembled, the port member is interchangeable with one of a plurality of other port members, each of the plurality of other port members having at least one of different dimensions, characteristics, components, and materials.

2. The modular vial adapter of claim 1, wherein, prior to assembly of the spike member, port member, and skirt member with one another, the spike member is interchangeable with one of a plurality of other spike members.

3. The modular vial adapter of claim 2, wherein the plurality of other spike members have at least one of different dimensions, characteristics, components, and materials.

4. The modular vial adapter of claim 1, wherein, prior to assembly of the spike member, port member, and skirt member with one another, the skirt member is interchangeable with one of a plurality of other skirt members.

5. The modular vial adapter of claim 4, wherein the plurality of other skirt members have at least one of different dimensions, characteristics, components, and materials.

6. The modular vial adapter of claim 1, wherein, when the spike member and port member are received in the recess, the position of distal tip of the spike member is maintained within the cavity for engagement with the vial seal upon receipt of the vial closure within the cavity of the skirt member.

7. The modular vial adapter of claim 6, wherein the connector assembly of the port member extends through the bore defined in the recess of the skirt member to thereby allow the connector assembly to be coupled to the delivery device for subsequent transport of fluid content from the vial.

8. The modular vial adapter of claim 6, wherein the at least one side wall comprises at least one detent extending from an inner surface thereof, the at least one detent is configured to engage the closure of the vial to retain the closure within the cavity once positioned therein.

9. The modular vial adapter of claim 6, wherein the skirt member comprises an external surface having one or more grip portions.

10. The modular vial adapter of claim 1, wherein the vent pathway allows for atmospheric air to enter the interior space of the vial to prevent negative pressure buildup when fluid content is transported from the vial via the fluid pathway provided by the first lumen.

11. The modular vial adapter of claim 1, further comprising a vent filter coupled to the second open end of the second lumen.

12. The modular vial adapter of claim 11, wherein the filter comprises a hydrophobic material having a pore size of 0.1 microns to 5 microns.

13. The modular vial adapter of claim 1, wherein the connector assembly of the port member comprises a delivery device-specific connection fitting, wherein the delivery device comprises a pump and/or injector assembly.

14. The modular vial adapter of claim 1, wherein the channel of the port member comprises a channel opening formed on a distal end thereof opposite the connector assembly and adjacent to the base, wherein the channel opening is shaped and/or sized to receive and retain a separately formed fluid filter membrane within.

15. The modular vial adapter of claim 14, wherein the filter comprises a material having a pore size of 5 microns to 150 microns.

16. The modular vial adapter of claim 1, wherein the skirt comprises at least one protrusion extending from a proximal end thereof and configured to engage a corresponding and mating geometry of a delivery device for maintaining alignment and limiting rotation of the assembled adapter in a visible, tactile, or audible manner.

* * * * *